United States Patent [19]
Seager et al.

[11] Patent Number: 6,105,823
[45] Date of Patent: *Aug. 22, 2000

[54] PRODUCT DISPENSER HAVING ROTATING BASE

[75] Inventors: Richard H. Seager, Mystic, Conn.; Peter Piscopo, Medford, N.J.

[73] Assignee: The Plastek Group, Erie, Pa.

[*] Notice: This patent is subject to a terminal disclaimer.

[21] Appl. No.: 09/201,506

[22] Filed: Nov. 30, 1998

Related U.S. Application Data

[63] Continuation-in-part of application No. 08/982,011, Dec. 1, 1995, Pat. No. 5,979,708.

[51] Int. Cl.$^7$ ..................................................... B67D 5/52
[52] U.S. Cl. ........................... 222/137; 222/386; 604/59
[58] Field of Search ..................... 222/386, 326, 222/327, 137, 145.5, 145.6; 604/15, 57, 59, 191

[56] References Cited

U.S. PATENT DOCUMENTS

| | | | |
|---|---|---|---|
| 5,289,949 | 3/1994 | Gentile | 222/137 |
| 5,979,708 | 11/1999 | Seager et al. | 222/137 |

*Primary Examiner*—Andres Kashnikow
*Assistant Examiner*—Sean P. O'Hanlon
*Attorney, Agent, or Firm*—Bachman & LaPointe, P.C.

[57] ABSTRACT

A product dispenser includes a housing defining an inner space for a product; a piston member movably disposed in the inner space for dispensing product from the inner space; a ram slidably associated with the housing for driving the piston in the inner space, and movable relative to the housing between an active position wherein the ram is aligned with the piston for dispensing product, and a neutral position wherein the ram is not aligned with the piston whereby the ram in the neutral position is slidable relative to the housing without dispensing product.

25 Claims, 5 Drawing Sheets

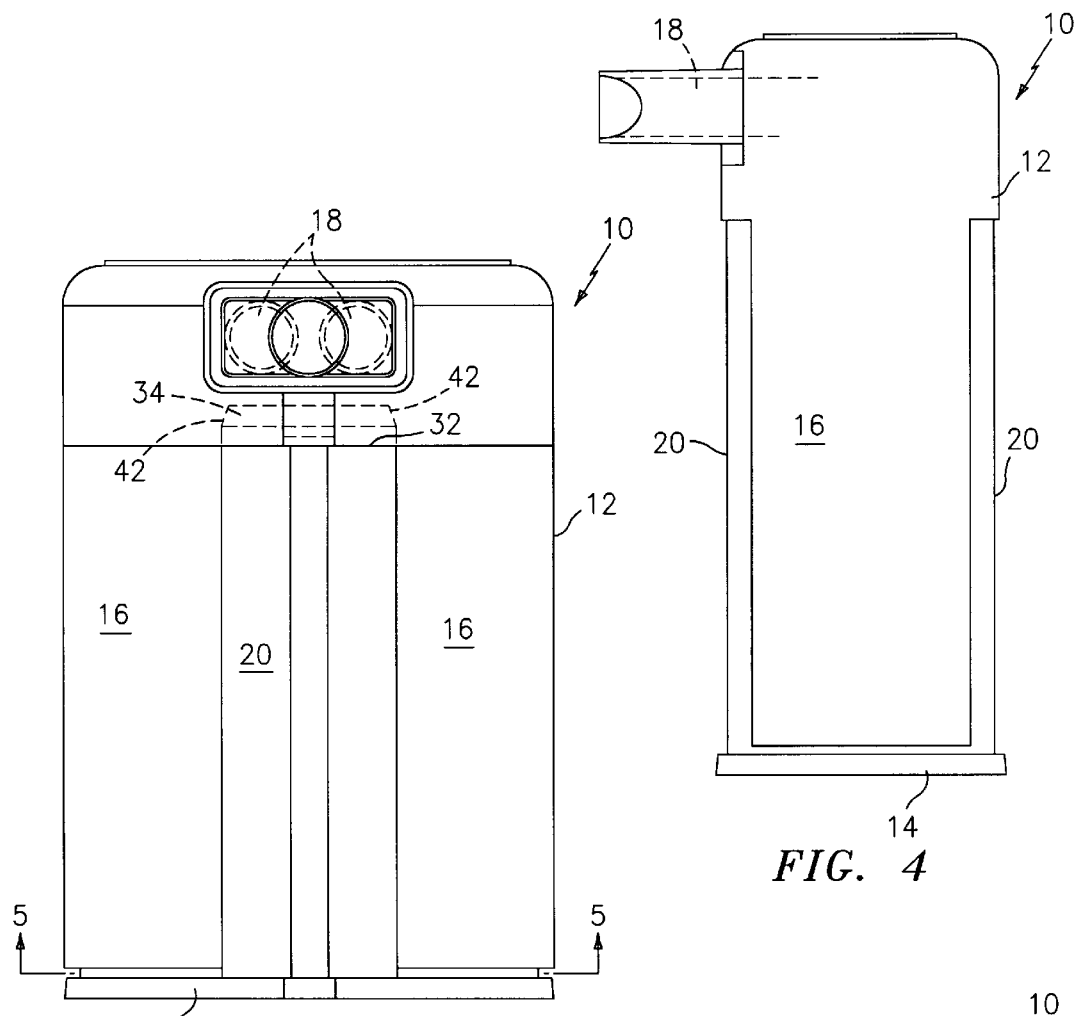
FIG. 3
FIG. 4
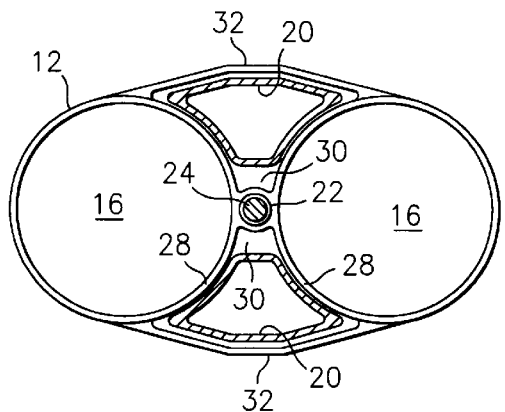
FIG. 5
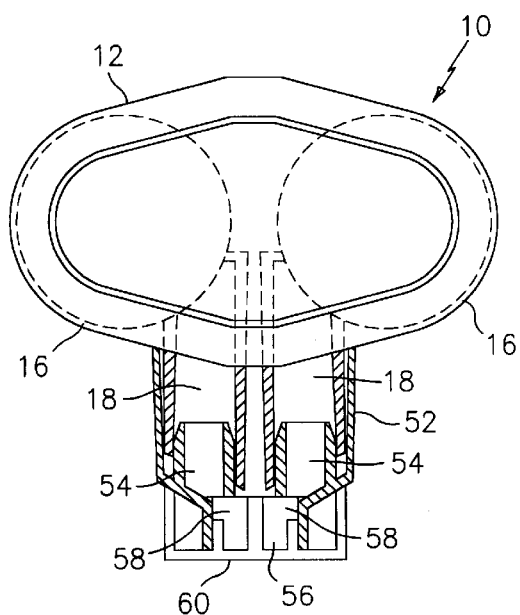
FIG. 9

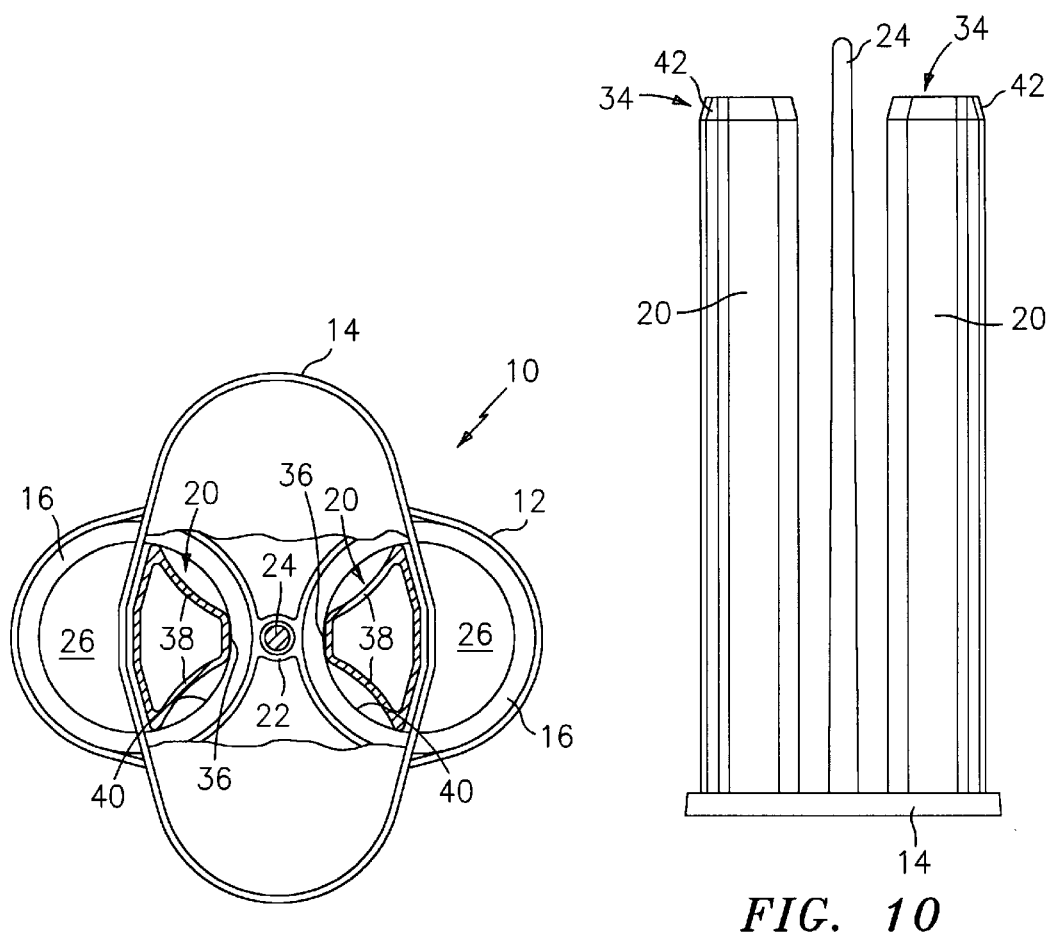
FIG. 8
FIG. 10
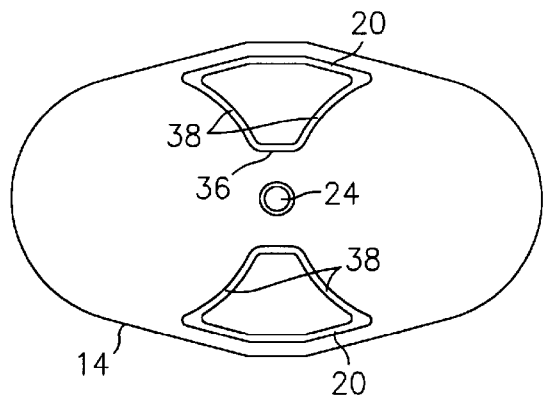
FIG. 11

PRODUCT DISPENSER HAVING ROTATING BASE

CROSS-REFERENCE TO RELATED APPLICATION

This application is a continuation-in-part of U.S. patent application Ser. No. 08/982,011, filed Dec. 1, 1997, now U.S. Pat. No. 5,979,708.

BACKGROUND OF THE INVENTION

The present invention relates to a product dispenser and, more particularly, to a product dispenser for dispensing extrudable product, especially product having components which must be kept separate until used.

Product dispensers are known for dispensing extrudable product such as toothpaste or other dental preparations wherein a combination of two substances or ingredients are provided. For example, U.S. Pat. No. 4,687,663 is drawn to an article for storage and delivery of baking soda and peroxide preparations and, as pointed out in this patent, the hydrogen peroxide and sodium bicarbonate may not normally be premixed.

U.S. Pat. No. 5,289,949 discloses a dispenser including a base and a housing/cartridge structure which slidably moves over the base portion. The product is contained in two cylinders in the upper housing structure. The base portion includes structures for driving product out of the cylinders, and the base must initially be in a fully extended position with respect to the housing so that product can be provided within the cylinders. However, this initial configuration results in the dispenser occupying a large amount of space which is undesirable during shipping, stocking, and even subsequent use.

The need remains for a product dispenser wherein the fully assembled dispenser containing product therein occupies less space.

It is therefore the primary object of the present invention to provide a dispenser wherein the base/ram structure can be fully advanced relative to the housing while cylinders contained within the housing are filled with product.

It is a further object of the present invention to provide a dispenser as above wherein the dispenser can be positioned to a shipping position which occupies substantially only the space occupied by the upper housing including cylinders containing product.

It is a still further object of the present invention to provide a dispenser as set forth above which can be readily configured by an end user to a position for simple, easy and stable use.

It is yet another object of the present invention to provide a dispenser as set forth above wherein an end user can easily re-position the dispenser to an original compact configuration for travel and the like.

Other objects and advantages will appear hereinbelow.

SUMMARY OF THE INVENTION

In accordance with the present invention, the foregoing objects and advantages are readily attained.

According to the invention, a product dispenser is provided which comprises a housing defining an inner space for a product; piston means movably disposed in the inner space for dispensing product from the inner space; a ram slidably associated with the housing for driving the piston means in the inner space, and movable relative to the housing between an active position wherein the ram is aligned with the piston means for dispensing product, and a neutral position wherein the ram is not aligned with the piston means whereby the ram in the neutral position is slidable relative to the housing without dispensing product.

In accordance with another aspect of the present invention, a product dispenser is provided which comprises a housing having at least one cylinder defining an inner product space; a base having at least one ram extending therefrom; and means for slidably and moveably connecting the housing and the base such that the base is slidable relative to the housing in a sliding direction, and is moveable relative to the housing substantially transverse to the sliding direction between an active position wherein the at least one ram is aligned with the inner product space of the at least one cylinder, whereby sliding the base relative to the housing in the sliding direction in the active position dispenses product, and the overall length of the dispenser in the neutral position is reduced.

BRIEF DESCRIPTION OF THE DRAWINGS

A detailed description of preferred embodiments of the present invention follows, with reference to the attached drawings, wherein:

FIG. 3 is a front view of a dispenser according to the present invention in the compact or closed position of FIG. 1;

FIG. 4 is a side view of the dispenser of the present invention in the compact or closed position of FIG. 1;

FIG. 5 is a sectional view taken along the lines 5—5 of FIG. 3;

FIG. 8 is a partially sectional bottom view of the dispenser of FIG. 6;

FIG. 9 is a top view of the housing of the dispenser of the present invention;

FIG. 10 is an end view of a base/ram structure in accordance with the present invention;

FIG. 11 is a top view of a base/ram structure in accordance with the present invention;

DETAILED DESCRIPTION

The invention relates to a product dispenser, especially a product dispenser for use in dispensing extrudable product, most preferably product having at least two components which must be maintained separate from each other until the product is to be used. One example of such a product is a toothpaste or dentifrice product which includes hydrogen peroxide and sodium bicarbonate. As set forth above, these product components are advantageous when combined, but cannot be mixed until they are to be used.

In accordance with the present invention, a product dispenser is provided which has a housing defining an internal space for containing the product, and a base including rams for driving product from the internal space, wherein the base and rams are slidable relative to the housing for dispensing product, and the rams are also movable or rotatable relative to the housing between an active position for dispensing product, and a neutral position wherein the base/rams can be fully advanced relative to the housing without dispensing product so as to position the product dispenser in a compact or fully advanced position which is particularly advantageous for the initial shipping of the product, and which is also advantageous subsequently for the end user who can reduce the size of the product, for example for travel purposes.

Figure 1:
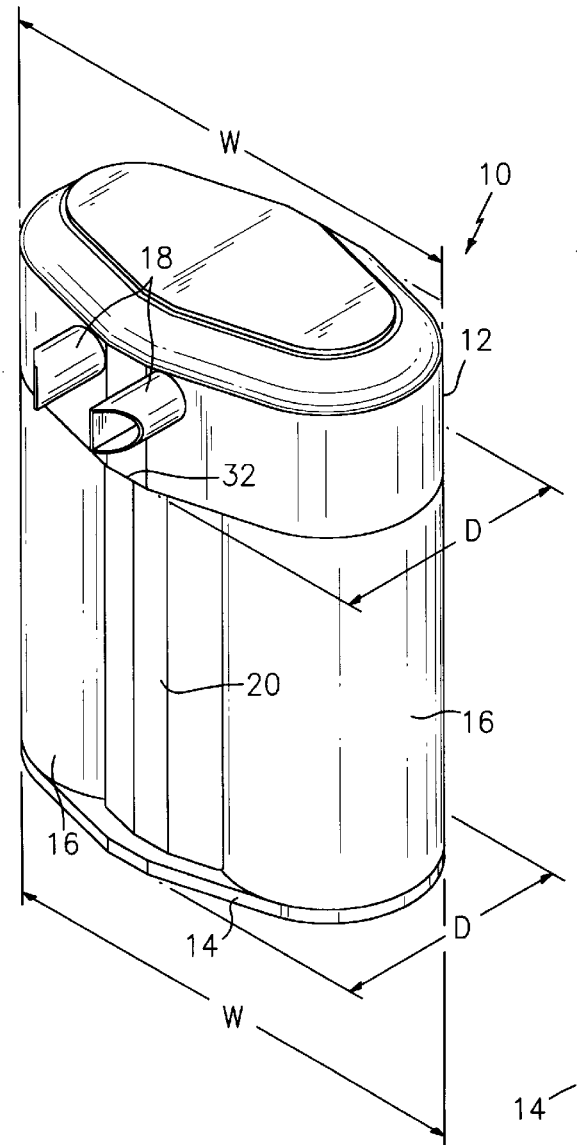
FIG. 1 is a perspective view of a dispenser in accordance with the present invention in a compact or shipping position.

Referring now to the drawings, a specific embodiment of the invention will be discussed. FIG. 1 shows a dispenser 10 in accordance with the present invention including a housing 12 and a base 14.

Housing 12 includes a wall structure defining an inner space, and preferably includes a wall structure defining one or more, in this case two, cylinders 16 for containing product therein. Housing 12 also preferably includes outlets 18 communicated with each cylinder 16, and product is dispensed through outlets 18 as will be further discussed below. Cylinders 16 may be substantially the same in diameter as shown, or may be of different size or diameter if desired, for example if it is desired to dispense product at a ratio of components other than 1:1.

Base 14 is preferably a substantially flat member adapted to provide stability for supporting dispenser 10, preferably in a substantially upright position as shown in FIG. 1. Extending from base 14 are one or more, preferably two, plungers or rams 20 which are adapted for use in driving product from cylinders 16 as will be further discussed.

Figure 2:
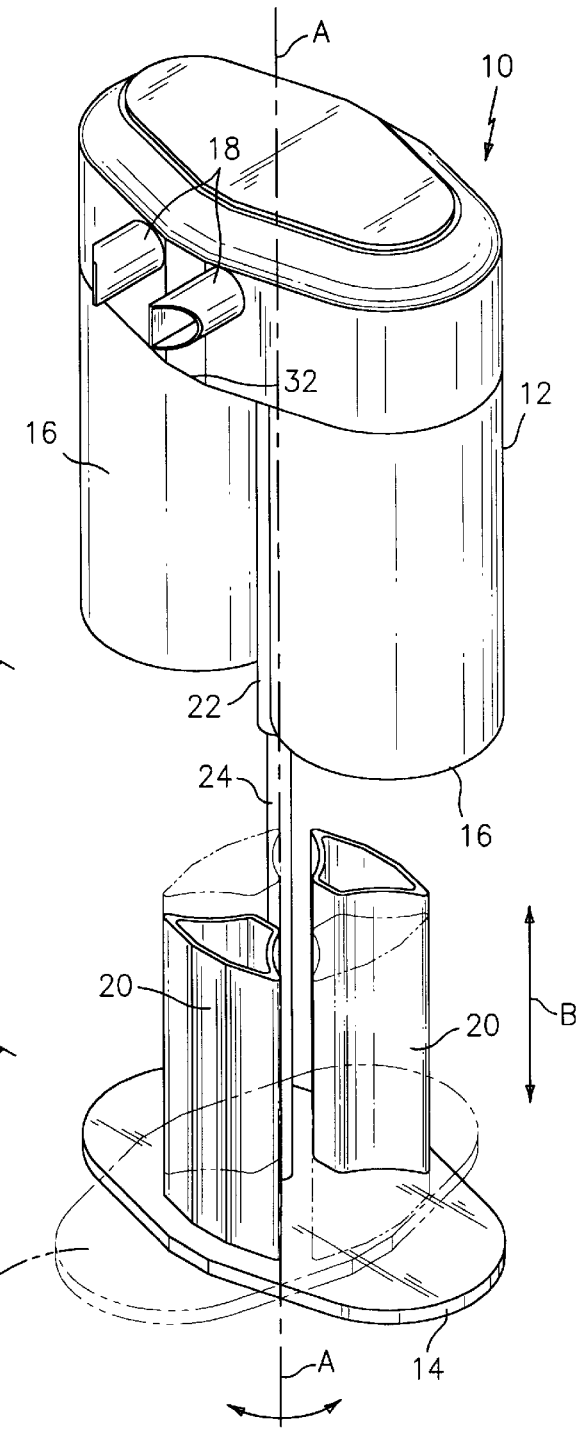
FIG. 2 is a perspective view of a dispenser in accordance with the present invention in an intermediate extended position.

Referring also to FIG. 2, base 14 and rams 20 in this embodiment are preferably slidably and rotatably connected to housing 12 such that base 14 and the rams 20 can be rotated relative to housing 12 around an axis of rotation A, and further so that rams 20 can slide along the axis of rotation as shown by arrow B (FIG. 2) between a fully extended position (FIG. 2) and an advanced position wherein base 14 and rams 20 are advanced along rotation axis A toward the fully closed position of FIG. 1.

As illustrated in FIG. 2, base 14 and rams 20 are rotatable around axis of rotation A between an active position, which is shown in dashed lines in FIG. 2 and which is further illustrated and described in connection with FIGS. 6 and 7, and a neutral position which is illustrated in FIG. 1 and in solid lines in FIG. 2. In the active position, rams 20 are substantially aligned with cylinders 16 such that translation or sliding along axis A as shown by arrow B results in sliding of rams 20 within cylinders 16 so as to dispense product from cylinders 16 as desired.

In the neutral position, rams 20 are positioned out of alignment with cylinders 16 as shown in solid lines in FIGS. 1 and 2 so that base 14 and rams 20 can be advanced to the compact position of FIG. 1 without dispensing product from cylinders 16.

Base 14 and rams 20 may be slidably and rotatably mounted to housing 12 as desired by the provision of a sleeve 22 mounted to or extending from housing 12 and extending substantially parallel to cylinders 16, and by providing a rod 24 mounted to base 14 and extending substantially parallel to rams 20, wherein rod 24 is adapted to slidably and rotatably fit within sleeve 22 to provide for the desired sliding and rotation of base 14 and rams 20 relative to housing 12. Of course, sleeve 22 could alternatively be mounted to base 14 while rod 24 could be mounted to housing 12, and numerous other mechanical connections could be provided for allowing the desired sliding and rotating of base 14 and rams 20 relative to housing 12. Further different structures could be used to slidably and moveably associate housing 12 and base 14 or rams 20. Such structure could provide for movement of rams 20 relative to cylinders 16 in other than rotating fashion, if desired, for example through linear translation as set forth below. It is also within the scope of the present invention to use no connecting structure, if desired, whereby housing 12 and base 14 or rams 20 could be separated and re-assembled in either the active or neutral positions.

It should be noted, however, that the structure for slidably connecting housing 12 and base 14 is advantageous in helping to provide good alignment between the elements and for keeping thrust centered during use of the dispenser, particularly where the cylinders contain product components having different viscosities.

In accordance with the foregoing, dispenser 10 of the present invention is particularly advantageous as compared to conventional dispensers of this type, wherein the ram structure must be positioned in a fully extended position when cylinders are filled with product. Such a prior art product configuration undesirably results in the dispenser occupying a larger space for shipping, or subsequent storage, particularly as compared to dispenser 10 of the present invention as shown in FIG. 1.

Referring now to FIG. 3, various features of dispenser 10 in accordance with the present invention will be further described. As shown, housing 12 is preferably a substantially elongate structure having a width W (FIG. 1) and depth D, and comprises cylinders 16 arranged substantially adjacent and parallel to each other as shown. As illustrated in FIG. 6, cylinders 16 also preferably each include a piston 26 slidably disposed therein for driving product from cylinder 16 out of outlet 18. Piston 26 is acted upon by rams 20 in the active position for driving product from dispenser 10 as will be discussed below.

Referring to FIG. 5, housing 12 has an outer surface 28 defining grooves or channels 30 for receiving rams 20 when base 14 and rams 20 are rotated to the neutral position. Housing 12 also preferably further includes a skirt 32 positioned around an upper portion thereof and overlapping channels 30 such that, when base 14 and rams 20 are in the fully advanced neutral position, ends 34 of rams 20 extend inside of skirt 32 as shown in FIG. 3. This advantageously serves to enhance dispenser stability and durability for shipping and the like. As clearly illustrated by FIGS. 2–5, as well as by FIG. 1, dispenser 10 in the fully advanced neutral position, or compact position, provides a dispenser fully loaded with product and having a height, width and depth which are substantially the same as the height, width and depth of housing 12 by itself.

Figures 6, 7:
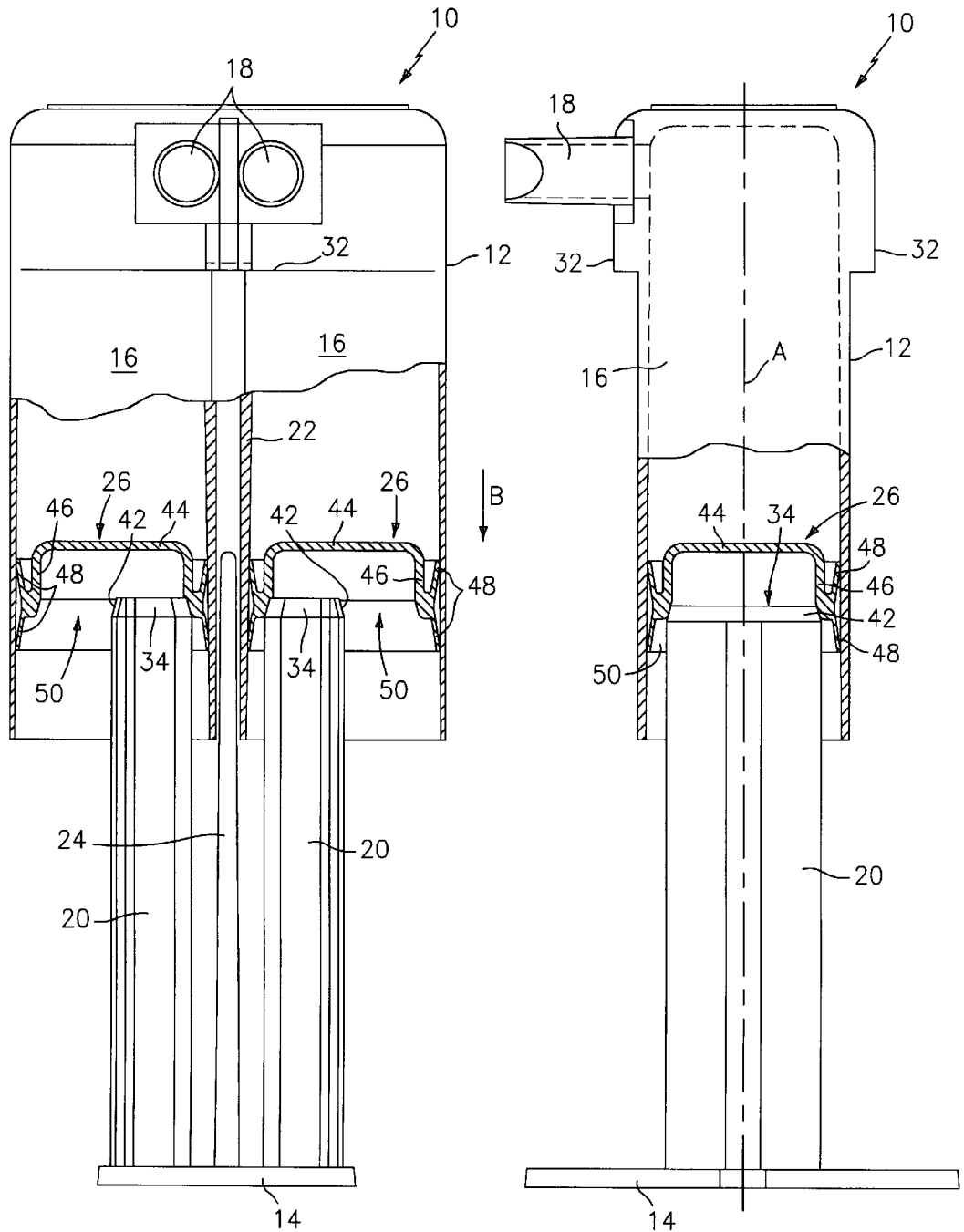
FIG. 6 is a front partially sectional view of a dispenser in accordance with the present invention in an extended active position.
FIG. 7 is a side view of the dispenser of the present invention in an extended active position.

Referring to FIG. 6, dispenser 10 in accordance with the present invention is shown with base 14 and rams 20 rotated to the active position wherein rams 20 contact piston 26 as desired. FIG. 6 also shows dispenser 10 with base 14 and rams 20 in a substantially extended position from which downward movement of housing 12 relative to base 14 and rams 20 as illustrated by arrow B results in downward movement of housing 12 relative to base 14, rams 20 and, accordingly, pistons 26. This results in relative upward movement of piston 26 within cylinders 16, thereby driving product out of outlets 18 as desired. FIG. 7 shows a side view of dispenser 10 in the position of FIG. 6, and further illustrates connection of outlets 18 to the inner space of cylinders 16.

Referring specifically to FIGS. 5 and 8, bottom views of dispenser 10 in accordance with the present invention are shown, rotated to the neutral position in FIG. 5 and rotated to the active position in FIG. 8. Advantageously, base 14 is substantially aligned with housing 12 in the neutral position as illustrated in FIG. 5 so as to minimize the size and profile of dispenser 10 as desired. In this position, the width and depth of base 14 are aligned with and substantially the same as the width and depth of housing 12 so as to advantageously reduce the profile of dispenser 10. In the active position, base 14 is turned at an angle relative to housing 12, preferably an angle of about 90° so as to be substantially perpendicular to housing 12 as shown in FIG. 8, and to thereby provide dispenser 10 with stability for use in the active position.

Still referring to FIG. 8, and referring also to FIGS. 10 and 11, rams 20 may suitably be two substantially upstanding ram members extending upwardly from base 14 in substantially parallel relationship, with rod 24 disposed therebetween as shown. As illustrated in FIG. 8, each ram 20 may suitably have a radial outward configuration consisting of a contour adapted to match the inner contour of skirt 32. Thus, as shown in FIG. 5, rams 20 snugly fit within channels 30 and inside of skirt 32 as desired.

Rams 20 also preferably have a roughly triangular shape oriented with a flat apex 36 positioned toward rod 24, and with arms 38 of the triangular shape extending from apex 36 being substantially arcuate so as to mate with the arcuate outer surface 28 of cylinders 16 as desired when rams 20 are positioned in the neutral position.

In the active position, and as illustrated in FIG. 8, rams 20 advantageously have a multiple-point contact relationship with an inner surface 40 of cylinders 16 so as to provide rams 20 with desirable stability during use to drive pistons 26 within cylinders 16. It is preferred that rams 20 have at least a two-point contact with inner surface 40 of cylinders 16, and preferably a three-point contact as illustrated in FIG. 8.

FIG. 11 illustrates base 14 with rams 20 and rod 24 extending therefrom in accordance with the invention. In further accordance with the invention, ends 34 of rams 20 may suitably be provided having angled or beveled edges 42 as shown so as to facilitate proper entry into cylinders 16 when in the active position, and proper entry into channels 30 when in the neutral position.

Referring to FIG. 6, it is preferred that pistons 26 be provided within cylinders 16, and that pistons 26 be driven by rams 20 to dispense product from cylinders 16. Pistons 26 preferably have a substantially flat base portion 44, a downwardly depending skirt portion 46 and flanges 48 for contacting inner surface 40 of cylinder 16 as desired. This structure advantageously provides for a sealing and slidable relationship between piston 26 and cylinders 16. Furthermore, this structure advantageously defines downwardly opening well 50 into which rams 20 extend when rams 20 are in the active position, extending into cylinders 16. Of course, pistons 26 may be provided having different shape or configuration as known to one of ordinary skill in the art.

Referring back to FIG. 3, and also to FIG. 9, housing 12 as shown preferably includes a plurality of outlets 18, in this case two, each communicating with a cylinder 16. In further accordance with the present invention, a nozzle member 52 may be provided having an inlet portion 54 adapted to connect with each outlet 18, and a single nozzle outlet 56 from which the combined product components are dispensed, as well as an intermediate manifold 58 for connecting inlet portion 54 to nozzle outlet 56. Nozzle member 52 may suitably be provided as a removable member slidably disposed over outlets 18, or as a permanent fixture of housing 12, and may further be provided with a cap member 60 (FIG. 9) for covering nozzle outlet 56 as desired.

In accordance with the present invention, housing 12 and base 14/rams 20 may suitably be provided of any material suitable to the desired end product. An example of a suitable material is polypropylene. Pistons 26 may suitably be made of any material providing the desired function of pistons 26. One example of suitable material from which pistons 26 can be provided is HDPE.

In accordance with the present invention, it should readily be appreciated that the provision of dispenser 10 including housing 12 and base 14/rams 20 both slidably and movably (transverse to axis A) connected to housing 12 advantageously provides for positioning dispenser 10 between an active position for use by an end user as desired, and a compact position wherein rams 20 are in a neutral position, and base 14 and rams 20 are substantially advanced relative to housing 12 such that rams 20 are exterior of, but overlap, cylinders 16. That is, in the compact position, rams 20 have a longitudinal axis which is parallel to and spaced from a longitudinal axis of cylinder 16.

Figure 12:
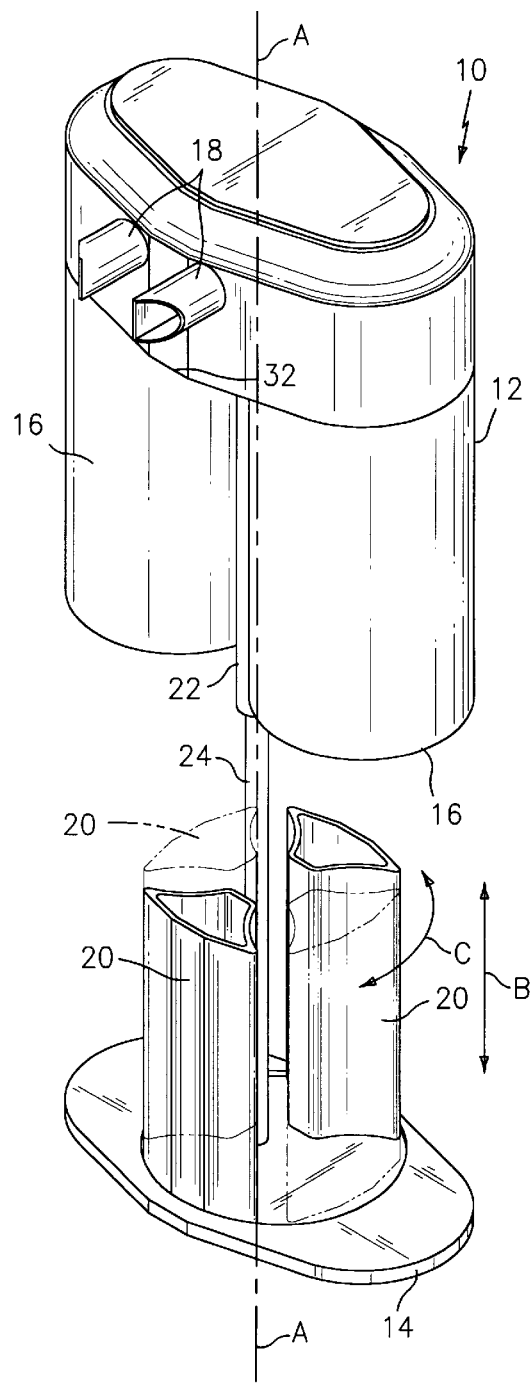
FIG. 12 is a perspective view of an alternative embodiment of the invention.

It should also be noted that dispenser 10 could be provided wherein only rams 20 are rotatable relative to housing 12, and wherein base 14 remains rotationally fixed relative to housing 12, all within the broad scope of the present invention. FIG. 12 shows an embodiment of the invention wherein rams 20 are rotatably mounted to base 14 such that rams 20 can be rotated around axis A between the active position and the neutral position while base 14 remains fixed relative to housing 12.

Figure 13:
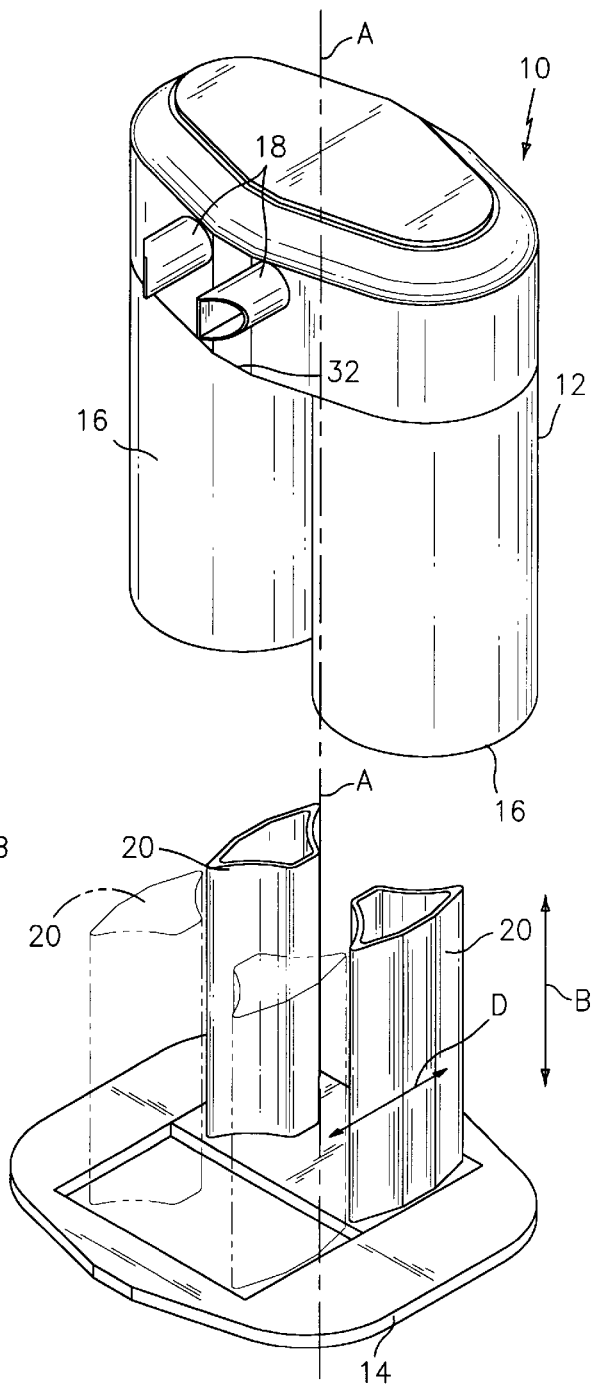
FIG. 13 is a perspective view of a further alternative embodiment of the invention.

FIG. 13 shows a further alternative embodiment of the invention wherein rams 20 are linearly moveable substantially transverse to axis A, rather than rotatable. In this embodiment, rams 20 can be moved or displaced substantially transverse to axis A between the neutral position and active position as desired. In this embodiment, as in the other embodiments, axis A is substantially parallel to a direction of sliding of rams 20 relative to housing 12 for either dispensing product in the active position or reducing height of the overall package in the neutral position. Further, movement of rams 20 between the active position and the neutral position is in a direction substantially transverse or perpendicular to axis A.

In the above embodiments, various structures are presented for both slidably and moveably (transverse to axis A) associating rams 20 with housing 12. As discussed, the sliding is a slidable association along axis A of rams 20 relative to cylinders 16 of housing 12. When rams 20 are in an active position, this sliding movement serves to drive product from cylinders 16 for dispensing as desired. When rams 20 are in the neutral position, such sliding serves to nest rams 20 relative to housing 12 for shipping and the like.

The moveable component of the association between rams 20 and housing 12 is movement in a direction which serves to position rams 20 between the active position wherein rams 20 are aligned with cylinders 16, and a neutral position wherein rams 20 are aligned away from cylinders 16 such that sliding movement substantially parallel to axis A can be performed so as to reduce the overall height of the package without dispensing product. This movement is, as set forth above, preferably substantially transverse to axis A.

It should also be noted that although housing 12 is disclosed and illustrated having cylinders 16 for containing product, the product space of housing 12 need not be cylindrical in shape, and could for example be square or some other shape, although a cylindrical shape as discussed herein is preferred.

In use, dispenser 10 is preferably originally shipped and sold in the compact position of FIG. 1. When it is desired to dispense product, housing 12 is pulled by the user away from base 14 and rams 20 to the fully extended position of FIG. 2, wherein rams 20 are withdrawn below the plane of cylinders 16 and can be rotated between the active and neutral positions. Rams 20 are then rotated into alignment with cylinders 16 in the active position as shown in FIGS. 6–8. In this configuration, downward force exerted on housing 12 drives housing 12 downward relative to base 14, rams 20 and pistons 26, thereby forcing product upward within cylinders 16 and out of outlets 18. Dispenser 10 may be left in this configuration until the product is exhausted, or dispenser 10 may be returned by the user to the compact position of FIG. 1, if desired, for example to facilitate storage or packing of dispenser 10.

Dispenser 10 is well suited to use in connection with toothpaste and dental preparations, especially those containing components which must not be mixed prior to dispensing for use. Of course, dispenser 10 according to the invention is also well suited to use in numerous other applications wherein extrudable product is to be dispensed.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

We claim:

1. A product dispenser, comprising:
    a housing defining an inner space for a product;
    piston movably disposed in the inner space for dispensing product from the inner space; and
    a ram slidably associated with the housing for driving the piston in the inner space, and movable relative to the housing between an active position wherein the ram is aligned with the piston for dispensing product, and a neutral position wherein the ram is not aligned with the piston whereby the ram in the neutral position is slidable relative to the housing without dispensing product.

2. A dispenser according to claim 1, wherein the ram is slidable relative to the housing in a sliding direction and is moveable substantially transverse to the sliding direction between the active position and the neutral position.

3. A dispenser according to claim 1, wherein the ram is rotatable relative to the housing around an axis of rotation which is substantially parallel to the sliding direction.

4. A dispenser according to claim 1, wherein the housing comprises a cylinder defining the inner space, the piston is slidably disposed in the cylinder, and the ram is slidable relative to the housing between an extended position wherein the ram is disengaged from the piston, and a closed position, wherein the ram is moveable in the extended position between the active position and the neutral position, and wherein sliding of the ram relative to the housing in the active position from the extended position toward the closed position moves the piston relative to the cylinder so as to dispense product, and wherein the ram is slidable in the neutral position from the extended position toward the closed position without moving the piston relative to the cylinder.

5. A dispenser according to claim 1, wherein the housing comprises two substantially parallel cylinders defining the inner space, and wherein the piston comprises a piston slidably disposed in each cylinder.

6. A dispenser according to claim 5, wherein the ram comprises two substantially parallel ram members aligned for translation within the cylinders in the active position, and aligned for translation outside the cylinders in the neutral position.

7. A dispenser according to claim 6, wherein the cylinders have a substantially circular inner surface, and wherein the ram members are shaped to provide at least two points of contact with said inner surface whereby the ram members are stabilized within the cylinders.

8. A dispenser according to claim 1, further comprising a base for supporting the dispenser, the ram being connected to the base.

9. A dispenser according to claim 8, wherein the housing and the base each have a substantially elongate shape having a width and a depth, wherein the width is larger than the depth, and wherein the width and depth of the base are substantially aligned with the width and depth of the housing in the neutral position.

10. A dispenser according to claim 9, wherein the housing has an outer surface including a recessed area aligned to receive the ram in the neutral position.

11. A dispenser according to claim 10, further comprising a sleeve member extending from one of the housing and the base, and a rod member sized to slidably fit within the sleeve member and extending from the other of the housing and the base whereby the ram and base are slidably and rotatably connected to the housing.

12. A dispenser according to claim 11, wherein the housing comprises two substantially parallel cylinders defining the inner space, and the ram comprises two substantially parallel ram members, and wherein one member of the sleeve member and the rod member is mounted between and parallel to the two cylinders, and the other member of the sleeve member and the rod member is mounted between and parallel to the two ram members.

13. A dispenser according to claim 8, wherein the ram is moveable relative to the housing and the base between the active position and the neutral position.

14. A dispenser according to claim 13, wherein the ram is rotatable relative to the housing and the base between the active position and the neutral position.

15. A dispenser according to claim 8, wherein the ram and the base are moveable relative to the housing between the active position and the neutral position.

16. A dispenser according to claim 15, wherein the ram and the base are rotatable relative to the housing between the active position and the neutral position.

17. A dispenser according to claim 1, further comprising an outlet connected to the housing and communicated with the inner space for dispensing product when the piston is advanced in the inner space.

18. A dispenser according to claim 17, wherein the housing comprises a plurality of cylinders defining the inner space in a plurality of discrete product space portions for containing separate product components, and wherein the outlet is communicated with each of the discrete product space portions.

19. A dispenser according to claim 18, wherein the outlet comprises a plurality of discrete outlet members each communicated with a single portion of the plurality of discrete product space portions, and further comprising a nozzle member having an inlet for communicating with each of the discrete outlet members, a single product outlet, and a manifold connecting the inlet to the outlet.

20. A dispenser according to claim 1, further comprising an extrudable product contained within the inner space, and wherein the ram is in the neutral position and advanced relative to the housing such that the ram is outside of and has a longitudinal axis parallel to and spaced from a longitudinal axis of the inner space.

21. A product dispenser, comprising:
a housing having at least one cylinder defining an inner product space;
a base having at least one ram extending therefrom; and
means for slidably and moveably connecting the housing and the base such that the base is slidable relative to the housing in a sliding direction, and is moveable relative to the housing substantially transverse to the sliding direction between an active position wherein the at least one ram is aligned with the inner product space of the at least one cylinder, and a neutral position wherein the at least one ram is aligned outside the inner product space of the at least one cylinder, whereby sliding the base relative to the housing in the sliding direction in the active position dispenses product.

22. A dispenser according to claim 21, further comprising a piston member disposed in each cylinder of the at least one cylinder, and wherein the at least one ram is aligned with the piston member in the active position.

23. A dispenser according to claim 21, wherein the base is slidable relative to the housing between an extended position wherein the at least one ram is substantially removed from the at least one cylinder, and a closed position wherein the at least one ram is advanced from the extended position relative to the at least one cylinder.

24. A dispenser according to claim 23, wherein the base is in the neutral position and fully advance to the closed position, and wherein the inner product space contains an extrudable product.

25. A dispenser according to claim 21, wherein the housing has an outer surface defining at least one channel, and wherein the at least one ram is adapted to slidably fit within the at least one cylinder in the active position and to slidably fit within the at least one channel in the neutral position.

* * * * *